United States Patent [19]

Lechevin et al.

[11] 4,156,714

[45] May 29, 1979

[54] RODENTICIDAL COMPOSITIONS

[75] Inventors: Jean-Claude Lechevin, Lyons; Jean N. Treilles, Lozanne, both of France

[73] Assignee: Lipha, Lyonnaise Industrielle Pharmaceutique, Lyons, France

[21] Appl. No.: 736,530

[22] Filed: Oct. 28, 1976

[30] Foreign Application Priority Data

Nov. 17, 1975 [FR] France .................. 75 34947

[51] Int. Cl.² .................................. A01N 17/14
[52] U.S. Cl. ....................................... 424/17
[58] Field of Search ............................. 424/17

[56] References Cited

U.S. PATENT DOCUMENTS

| | | | |
|---|---|---|---|
| 2,687,365 | 8/1954 | Link | 424/17 |
| 2,813,058 | 11/1957 | Smith | 424/17 |
| 2,957,804 | 10/1960 | Shuyler | 424/17 |

FOREIGN PATENT DOCUMENTS

| | | |
|---|---|---|
| 627090 | 4/1963 | Belgium. |
| 2158880 | 7/1972 | Fed. Rep. of Germany. |
| 802781 | 9/1936 | France. |
| 992824 | 10/1951 | France. |
| 1267950 | 6/1961 | France. |
| 31-6450 | 7/1956 | Japan. |
| 33-1226 | 2/1958 | Japan. |
| 48-00056 | 1/1973 | Japan. |
| 6603111 | 9/1966 | Netherlands. |
| 1026823 | 4/1966 | United Kingdom. |
| 1036965 | 7/1966 | United Kingdom. |

OTHER PUBLICATIONS

Chitty et al., "Control of Rats and Mice", vol. II, Rats, (1954) Oxford, pp. 352–373, 500–527.
Chitty et al. "Control of Rats and Mice", vol. III, House Mice, (1954) Oxford, pp. 99–115
Trademark Reg. No. 1,009,829 Reg. May 6, 1975, "TOX-HID" Wisconsin Alumni Research Foundation, for Rodenticides which have been coated with Film-forming Materials.

*Primary Examiner*—Shep K. Rose
*Attorney, Agent, or Firm*—Browdy & Neimark

[57] ABSTRACT

A rodenticidal composition comprises a carrier edible by rodents, the surfaces of the pieces of said carrier being coated with a film comprising a film-forming substance and a toxic substance which reduces the level of prothrombin in the blood of a rodent. The compositions are particularly suitable for destroying rats and mice.

4 Claims, No Drawings

RODENTICIDAL COMPOSITIONS

This invention relates to new rodenticidal compositions intended for destroying rodents such as rats and mice.

DESCRIPTION OF THE PRIOR ART

It is known that a number of derivatives of the indandiones and of 4-hydroxycoumarins have the property of lowering the level of prothrombin in the blood and for this reason can be used as rat poisons since they cause a high mortality among rodents as a result of internal hemorrhages. Other toxic substances may also be used.

Usually, the toxic substance is mixed with a carrier which rodents will eat, such as a cereal. In one technique which is employed, the cereal is oiled and then sprinkled with powdered talc containing the poison. However, baits prepared by this method suffer from the drawback that their power to attract decreases with passage of time, i.e. they age.

SUMMARY OF THE INVENTION

In accordance with the invention, rodenticidal compositions having an improved appearance have been discovered which retain their power to attract rodents irrespective of the age of the composition.

These rodenticidal compositions of the invention are baits based upon a carrier which rodents will eat, the surface of said baits being coated with a film-forming agent which contains the toxic substance.

DETAILED DESCRIPTION OF THE INVENTION

The invention is applicable to all toxic substances useful for the destruction of rodents, and in particular to the anticoagulant substances such as (a) the derivatives of 4-hydroxycoumarin: 3-(1-phenyl-2-acetyl)ethyl-4-hydroxycoumarin ("Warfarin"), 3-(α-acetonyl-4-chlorobenzyl)-4-hydroxycoumarin ("Coumachlore"), 1'-[3-(4'-hydroxycoumarinyl-3')-3-phenyl-1-(4'-bromobiphenyl-4')]propan-1-ol ("Bromadiolone"), 3-(3'-paradiphenylyl-1',2',3',4'-tetrahydronaphthyl-1)-4-hydroxycoumarin ("Difenacoum"), and 3-(1',2',3',4'-tetrahydronaphthyl-1')-4-hydroxycoumarin ("Coumatetralyl"), (b) the derivatives of the indandiones such as 1,1-diphenyl-2-acetyl-1,3-indandione ("Diphacinone") and (1'-parachlorophenyl-1'-phenyl)-2-acetyl-1,3-indandione ("Chlorodiphacinone"), and (c) 2-chloro-4-dimethylamino-6-methyl pyrimidine ("Crimidine").

The film-forming substances used may be polymers, such as polymers of vinyl acetate and acrylic polymers, the film-forming polyethylene glycols, and film-forming derivatives of cellulose, more especially ethylcellulose and hydroxypropylmethylcellulose.

The baits intended for coating may be selected from cereals such as wheat, hulled oats, maize, barley or any other carrier eaten by rodents such as millet grains and synthetic pellets.

The rodenticidal compositions are obtained by a new method for preparing baits, by coating the surface of the bait with a solution in a suitable volatile solvent of the toxic substance and of the film-forming agent.

When the solvent has evaporated, the toxic substance remains held within the film of film-forming substance which has been deposited upon the surface of the individuals baits.

The volatile solvents used to prepare the solutions of toxic substance and film-forming agent are selected from alcohols, ketones, esters and chlorinated hydrocarbons. If desired, additional non-volatile solvents may also be used to act as tertiary solvents or co-solvents, such as dimethyl sulfoxide.

The solutions of toxic substance and film-forming substance are simply prepared by dissolving the substances under cold conditions. The solutions may also be flavored and/or colored.

The baits are coated by pouring a solution of the toxic substance and of the film-forming agent over the surfaces thereof whilst they are maintained in continuous and regular motion in a suitable device such as a mixer.

This new method is advantageous insofar as the toxic substance is concerned in view of its special location in the bait, which markedly facilitates the quantitative determination of the toxic substance in the bait, and insofar as the bait is concerned by reason of its appearance and the protection which is provided by the film-forming substance.

Moreover, because the bait is coated, this new method of preparation enables a more uniform appearance to be secured which is particularly noticeable when the bait is colored.

In addition, the bait is protected from influence by its surroundings thus enabling it better to retain its organoleptic properties and, in particular, its power to attract, as the following table shows in which a comparison is made between the attracting power of a bait (1) which was prepared using "chlorodiphacinone" by the method of the present invention (the technique used in Example 4) and another bait (2) which was prepared by a conventional method (100 kg of corn was oiled with 2 liters of paraffin oil and then sprinkled with 5 kg of a powder containing 99.9% by weight of talc and 0.1% by weight of chlorodiphacinone).

The tests were carried out upon batches of 10 rats (Ratus norvegicus) using animals of as uniform a weight as possible kept in individual cages. The baits to be compared were placed in two identical feed-holders which contained equal quantities of (1) and (2).

The positions of the feed-holders were reversed each day in order to prevent the results being affected by a preference on the part of an animal for a feed-holder located in a particular position. Each day, for a period of three days, the amount of each of the two baits consumed was determined by weighing in order to determine which bait the animals preferred.

The trials were carried out with freshly prepared baits and with baits which had been prepared twelve months prior to the tests and stored.

|  | Mean Daily Consumption per Rat per Day in grams | | | | | |
| --- | --- | --- | --- | --- | --- | --- |
|  | Bait No. 1 according to the invention | | | Conventinal Bait No. 2 | | |
|  | Day 1 | Day 2 | Day 3 | Day 1 | Day 2 | Day 3 |
| Freshly Prepared Bait | 9 | 10 | 10 | 9 | 9.5 | 7.5 |
| Bait Prepared 12 months previously and stored | 12 | 15.5 | 13 | 5 | 6.5 | 5 |

Although there is no significant difference between the two baits when both were used in freshly prepared form, it can, on the other hand, be seen that the animals show a marked preference for the bait (1) prepared in accordance with the invention when the baits have been aged.

In addition, the physical characteristics of the bait and the ease with which it can be handled are improved. In particular, as a result of the improvement in the free-flowing properties of the bait, bagging and packaging operations are simplified.

Moreover, the poison, which is deposited upon the surface of the bait, is to a large extent, protected from the physical and chemical effects of the other ingredients of the bait. In addition to other advantages, the remote possibility of more or less labile bonds forming between the poison and the other ingredients of the bait enables a simple extractive technique to be used when determining the quantity of the poison present thus ensuring a quantitative extraction and minimizing interference caused by the other ingredients of the bait. Normally, it is enough to extract the poison with a solvent which dissolves both the poison and the film-forming agent, without any special preliminary treatment, such as by grinding which is required when the poison is distributed throughout the mass of the bait and which is a considerable hindrance when using analytical techniques.

DESCRIPTION OF THE PREFERRED EMBODIMENTS

The following examples illustrate the preparation of typical rodenticides in accordance with the invention.

EXAMPLE 1

The preparation of wheat poisoned with "Bromadiolone".

500 g of polyvinyl acetate and then 10 g of rhodamine are dissolved in three liters of methylene chloride. 5 g of "Bromadiolone" previously dissolved in 60 ml of dimethyl sulfoxide is added to this solution. The mixture obtained is distributed over the surfaces of 100 kg of wheat grains.

EXAMPLE 2

The preparation of hulled oats poisoned with "Bromadiolone" is carried out as described in Example 1 substituting hulled oats for the wheat used in that Example.

EXAMPLE 3

The preparation of millet grains poisoned with "Bromadiolone" is carried out as described in Example 1 substituting millet grains for the wheat used in that Example.

EXAMPLE 4

The preparation of wheat poisoned with "Chlorodiphacinone".

200 g of ethyl cellulose, 5 g of "Chlorodiphacinone", and then 10 g of rhodamine are dissolved in 3 liters of methylene chloride.

The solution obtained is distributed over the surfaces of 100 kg of wheat grains.

EXAMPLE 5

The preparation of wheat poisoned with "Crimidine".

200 g of a polyacrylic resin of high molecular weight, 100 g of "Crimidine", and then 10 g of rhodamine are dissolved in three liters of methylene chloride. The solution obtained is distributed over the surfaces of 100 kg of wheat grains.

EXAMPLE 6

The preparation of wheat poisoned with "Diphacinone".

500 g of polyvinyl acetate, 5 g of "Diphacinone" and then 10 g of rhodamine are dissolved in three liters of methylene chloride. The solution obtained is distributed over the surfaces of 100 kg of wheat grains.

EXAMPLE 7

The preparation of wheat poisoned with "Difenacoum".

200 g of ethyl cellulose, 5 g of "Difenacoum" and then 10 g of rhodamine are dissolved in 3 liters of methylene chloride. The solution obtained is distributed over the surfaces of 100 g of wheat grains.

We claim:

1. A rodenticidal composition including a cereal carrier and a toxic substance in which the toxic substance is not in direct physical contact with the bait and in which the composition is capable of retaining the organoleptic properties of the carrier and the power to attract, even after storage, consisting essentially of an oil-free cereal carrier of wheat, hulled oats, millet, or any other cereal grain edible by rodents which otherwise are not as attractive to rodents when aged and stored twelve months as when freshly prepared, the surface of the individual grains of said carrier being coated with a film consisting essentially of a film-forming substance and a toxic substance, within said film, which reduces the level of prothrombin in the blood of a rodent, said film-forming substance being selected from the group consisting of film-forming polymers of vinyl acetate, film-forming acrylic polymers, film-forming cellulose derivatives and film-forming polyethylene glycols, said composition enabling a single extractive technique, of extracting the poison with a solvent which dissolves both the poison and the film-forming agent, to be used when determining the quantity of the poison present, thus ensuring a quantitative extraction, and minimizing interference caused by any additional ingredients of the bait.

2. The composition of claim 1 in which said toxic substance is a rodenticidal derivative of 4-hydroxycoumarin.

3. The composition of claim 1 in which said toxic substance is a rodenticidal derivative of an indandione.

4. The composition of claim 1 in which said toxic substance is 2-chloro-4-dimethylamino-6-methylpyrimidine.

* * * * *